(12) United States Patent
Cutino

(10) Patent No.: US 11,419,622 B2
(45) Date of Patent: Aug. 23, 2022

(54) AUTOMATED DEVICE FOR CHOKING

(71) Applicant: Mark Anthony Cutino, Bremerton, WA (US)

(72) Inventor: Mark Anthony Cutino, Bremerton, WA (US)

( * ) Notice: Subject to any disclaimer, the term of this patent is extended or adjusted under 35 U.S.C. 154(b) by 0 days.

(21) Appl. No.: 15/818,247

(22) Filed: Nov. 20, 2017

(65) Prior Publication Data

US 2019/0150962 A1    May 23, 2019

(51) Int. Cl.

| | |
|---|---|
| *A61B 17/24* | (2006.01) |
| *A61B 17/50* | (2006.01) |
| *A61B 1/05* | (2006.01) |
| *A61B 1/06* | (2006.01) |
| *A61B 17/00* | (2006.01) |
| *A61B 17/30* | (2006.01) |
| *A61M 16/04* | (2006.01) |

(52) U.S. Cl.
CPC ............... *A61B 17/24* (2013.01); *A61B 1/05* (2013.01); *A61B 1/06* (2013.01); *A61B 17/50* (2013.01); *A61B 2017/00022* (2013.01); *A61B 2017/00115* (2013.01); *A61B 2017/00398* (2013.01); *A61B 2017/00561* (2013.01); *A61B 2017/00734* (2013.01); *A61B 2017/00889* (2013.01); *A61B 2017/306* (2013.01); *A61M 16/049* (2014.02)

(58) Field of Classification Search
CPC ..................... A61B 17/24; A61B 17/50; A61B 2017/00561; A61M 1/009; A61M 1/0011; A61M 1/0023; A61M 16/00; A61M 16/0057; A61M 16/006; A61M 16/0063; A61M 16/0066; A61M 16/0072; A61M 16/0075; A61M 16/0078; A61M 16/0081; A61M 16/0084; A61M 16/003; A61M 1/00; A61M 1/0031; A61M 1/0033; A61M 1/0088; A61M 1/0092; A61M 1/90; A61M 1/962; A61M 1/964

See application file for complete search history.

(56) References Cited

U.S. PATENT DOCUMENTS

| | | | |
|---|---|---|---|
| 8,317,774 B2 * | 11/2012 | Adahan | A61M 1/0088 604/313 |
| 10,384,041 B2 * | 8/2019 | Patel | A61M 1/0066 |
| 2013/0165821 A1 * | 6/2013 | Freedman | A61F 13/0279 601/2 |
| 2014/0336533 A1 * | 11/2014 | Dardenne | A61F 15/008 600/573 |
| 2016/0317725 A1 * | 11/2016 | Berry | A61M 1/0035 |
| 2019/0076298 A1 * | 3/2019 | Quintanar | A61F 13/00055 |

\* cited by examiner

*Primary Examiner* — Sarah A Simpson
(74) *Attorney, Agent, or Firm* — Seattle Patent Group LLC; James Haugen

(57) ABSTRACT

Techniques for blockage removal is provided, which may provide immediate and effective aid to a choking victim. A blockage removal device may comprise a mouthpiece disposed on an inlet. The inlet may be coupled to a chamber configured to hold a vacuum generated by a vacuum pump. A pressure transducer may send information about the vacuum to an electronic control unit (ECU). The ECU may send the information to a solenoid valve, which may open and close at a predetermined setting, instantly exposing or blocking the vacuum.

3 Claims, 3 Drawing Sheets

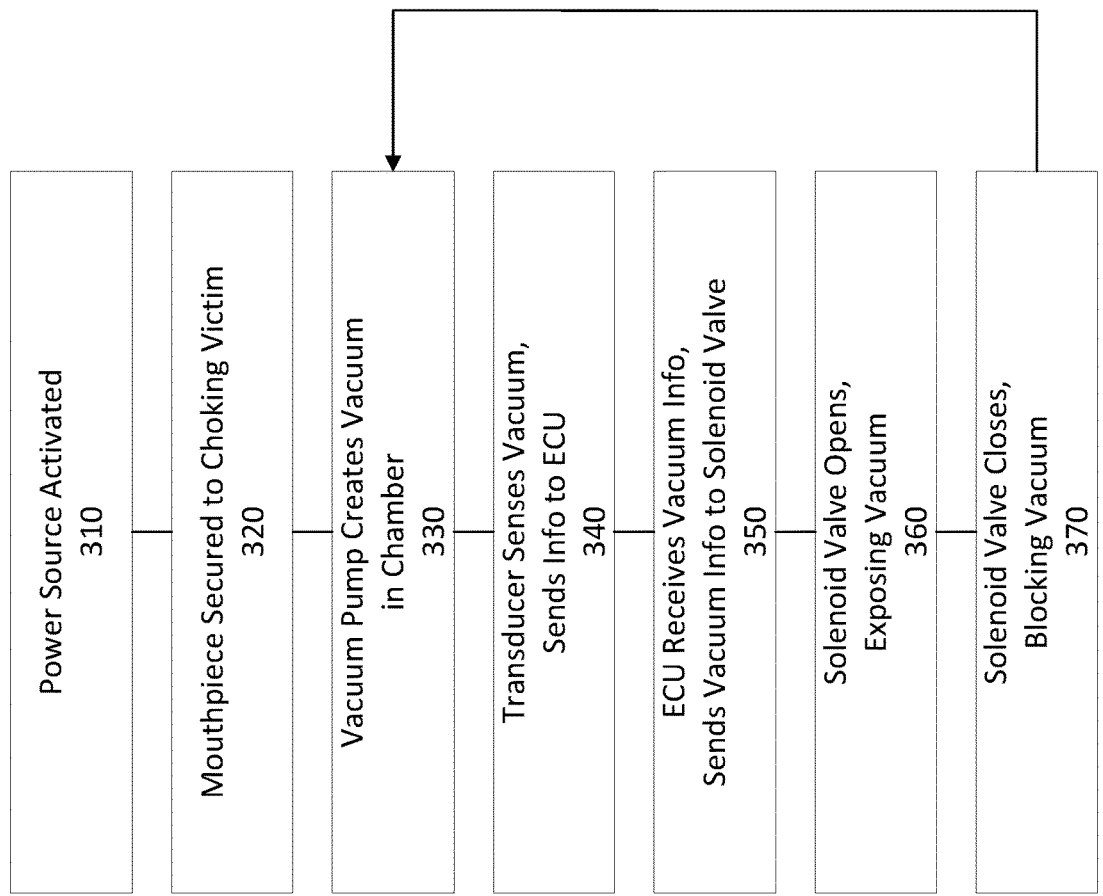

AUTOMATED DEVICE FOR CHOKING

FIELD

This disclosure relates generally to blockage removal.

BACKGROUND

Choking is a common occurrence which may become a life-threatening situation if not resolved quickly. Choking may entail the mechanical obstruction of the flow of air from the environment into the lungs. Choking may occur when an airway becomes constricted or obstructed, for example, when a foreign object lodges in a throat or windpipe.

Choking may be partial or complete. Partial choking may allow some, but insufficient, air flow into the lungs, whereas complete choking may cut off air flow entirely. Because choking deprives a brain of oxygen, immediate aid is crucial. Prolonged or complete choking may result in asphyxia, which may lead to anoxia or death. Conventional methods to aid a choking victim, for example, abdominal thrusts, chest thrusts, cardiopulmonary resuscitation (CPR), or using a finger to dislodge an obstruction are often inadequate and insufficient in adapting to a rescuer's or victim's particular physical conditions or limitations.

SUMMARY

The following presents a simplified summary of the disclosure to provide a basic understanding to the reader. This summary is not an extensive overview of the disclosure, nor does it identify key or critical elements of the claimed subject matter or define its scope. Its sole purpose is to present some concepts disclosed in a simplified form as a precursor to the more detailed description that is later presented.

The instant application discloses, among other things, blockage removal, which may provide ways to remove a blockage from a passageway. For example, if a person is choking, this device may help dislodge an item from an airway. In one implementation, blockage removal may comprise a mouthpiece coupled to a chamber configured to hold vacuum generated by a vacuum pump. A pressure transducer may sense an amount of vacuum, for example, and send the information to an electronic control unit (ECU). The ECU may send the information to a solenoid valve, which may open at a predetermined setting, instantly exposing the vacuum. The solenoid valve may close at a predetermined setting, blocking the vacuum. The blockage removal process may start over again at 10-second intervals, or another duration, for example, or until full or partial vacuum has been achieved, a victim's airway has been cleared, or choking has been resolved.

Many of the attendant features may be more readily appreciated as they become better understood by reference to the following detailed description considered in connection with the attached drawings.

BRIEF DESCRIPTION OF THE DRAWINGS

FIG. 3 illustrates a flow diagram of a Blockage Removal process, according to one embodiment.

Like reference numerals are used to designate like parts in the accompanying drawings.

DETAILED DESCRIPTION

Figure 1:
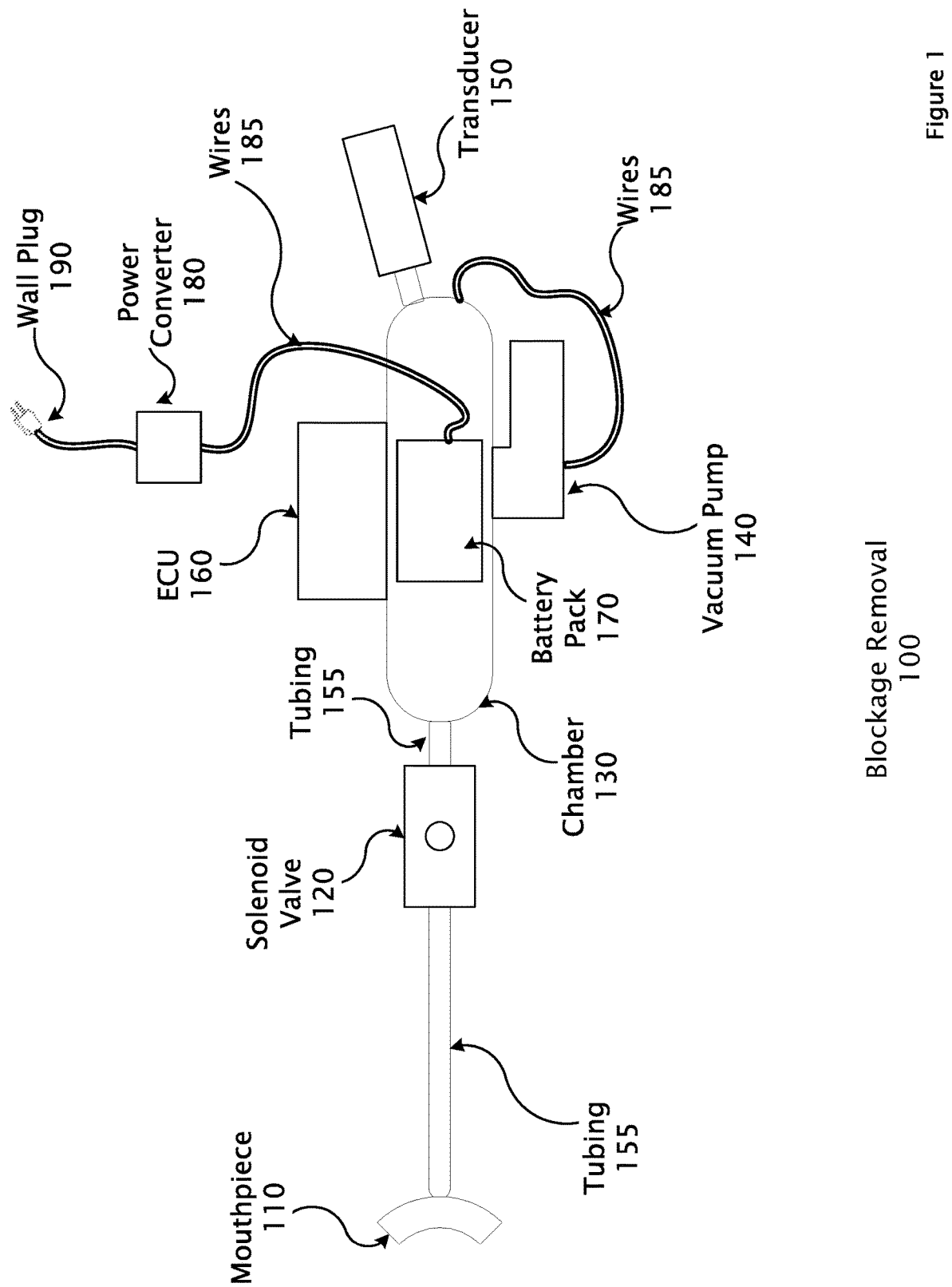
FIG. 1 illustrates a diagrammatic top view of a Blockage Removal device, according to one embodiment.

A more particular description of certain implementations of Multi-Author Document Collaboration may be had by references to the implementations shown in the drawings that form a part of this specification, in which like numerals represent like objects.

The illustrated operations in the description show certain events occurring in a certain order. One skilled in the art will recognize that certain operations may be performed in a different order, modified or removed. Moreover, steps may be added to the described logic and still conform to the described implementations.

FIG. 1 illustrates a diagrammatic top view of a Blockage Removal 100 device, according to one embodiment. In one implementation, it may comprise an inlet upon which Mouthpiece 100 is disposed and coupled to Chamber 130 by Tubing 155. Chamber 130 may comprise an evacuated cylinder configured to hold vacuum generated by Vacuum Pump 140. Transducer 150 may comprise a pressure transducer operable to sense an amount of vacuum inside of Chamber 130. Transducer 150 may send information about the vacuum to an electronic control unit, ECU 160, or a computer, which may send information to a pressure read-out. In another embodiment, ECU 160 may include a pressure read-out.

ECU 160 may send the vacuum information to Solenoid Valve 120, which may be disposed between Mouthpiece 110 and Chamber 130. Solenoid Valve 120 may couple to Mouthpiece 110 and Chamber 130 by Tubing 155. Solenoid Valve 120 may use electricity to open at a predetermined setting, instantly exposing the vacuum, enabling an instantaneous jolt or change in pressure conducive to quickly and safely removing an obstruction from a passageway, for example, dislodging a foreign object from an airway of a victim of complete or partial choking, or resolving a choking incident without causing further discomfort, damage, or injury. Solenoid Valve 120 may close at a predetermined setting, blocking the vacuum, and the cycle may start over again at 10 second intervals or another duration, or until full or partial vacuum has been achieved, a victim's airway has been cleared, an obstruction has been removed, or choking has been resolved, for example.

Chamber 130 may couple to a power source such as Battery Pack 170, Wall Plug 190, or Power Converter 180, which may comprise an alternating current (AC) to direct current (DC) converter to allow the system to run off the battery independently. In another implementation, Blockage Removal 100 may operate by other power sources, for example, solar power. The power sources of Blockage Removal 100 may couple to one another, or other components of Blockage Removal, by Wires 185, through which electricity may pass.

A person skilled in the art will understand that Blockage Removal 100 or its components may comprise various shapes, colors, or sizes, and may be made of any material, for example, polymers, composites, wood, rubber, metal, or other materials.

Figure 2:
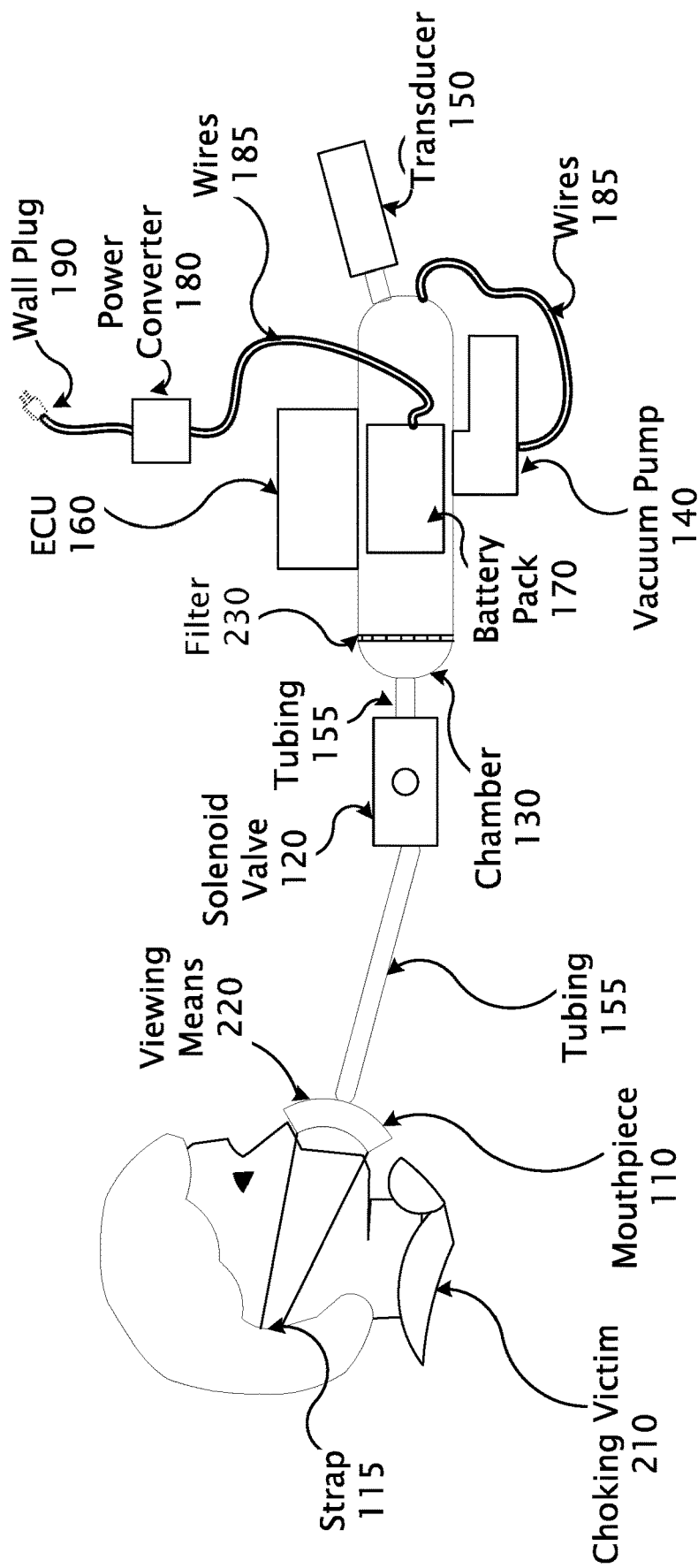
FIG. 2 illustrates a diagrammatic perspective view of a Blockage Removal device utilized on a choking victim, according to one embodiment.

FIG. 2 illustrates a diagrammatic perspective view of a Blockage Removal 100 device utilized on a choking victim, according to one embodiment. Blockage Removal 100 may be operable to provide immediate and effective aid to Choking Victim 210. Choking Victim 210 may comprise a person or animal whose airway is constricted or obstructed, for example, because of a foreign object has entered a throat or windpipe. Choking Victim 210 may also include any non-living thing which otherwise experiences blockage of a passageway. In one implementation, a user may place Mouthpiece 110 over an opening, for example, a mouth, of Choking Victim 210. Mouthpiece 110 may create an airtight or watertight seal around the mouth of Choking Victim 210. In another implementation, a Strap 115 or other attachment means may facilitate securing of Mouthpiece 110, Blockage Removal 100, or any of its components to Choking Victim 210.

Mouthpiece 110 may be disposed on an inlet of Blockage Removal 100. Mouthpiece 110 may couple to Chamber 130 by Tubing 155, which may be disposed between Mouthpiece 110 and Chamber 130. Tubing 155 may comprise a clear or translucent material which may allow a user to see and determine whether an obstruction has been removed from an airway of Choking Victim 210, for example. Tubing 155 may be disposed at any angle.

Chamber 130 may comprise an evacuated cylinder configured to hold a vacuum generated by Vacuum Pump 140. In one implementation, Vacuum Pump 140 may contain an impeller which uses centrifugal force to generate the vacuum. In another embodiment, Vacuum Pump 140 may be operable to generate a positive displacement of volume, for example.

Transducer 150 may comprise a pressure transducer operable to sense an amount of vacuum inside of Chamber 130. Transducer 150 may send information about the vacuum to an electronic control unit, ECU 160, or a computer, which may include a pressure read-out. In order to prevent injury, for example, damage to a trachea or larynx of Choking Victim 210, a plurality of settings related to an amount of vacuum stored in the chamber may be pre-programmed into the ECU 160. In another implementation, a plurality of settings related to factors from the list containing a victim's condition, a victim's characteristics, or environmental condition, for example, may be pre-programmed into ECU 160. For example, the amount of force required to dislodge an obstruction in the airway of a young child or small adult may be significantly less than that required by a full-grown adult or large individual.

ECU 160 may send the vacuum information to Solenoid Valve 120, which may be disposed between Mouthpiece 110 and Chamber 130, for example, on Tubing 155. Solenoid Valve 120 may use electricity to open at a predetermined setting, instantly exposing the vacuum. Solenoid Valve 120 may close at a predetermined setting, blocking the vacuum, and the cycle may start over again at 10 second intervals or another duration, for example, or until full or partial vacuum has been achieved, a victim's airway has been cleared, an obstruction has been removed, or choking has been resolved.

Instead of utilizing a constant stream of negative pressure found in conventional vacuum devices, Blockage Removal 100 may achieve an instantaneous jolt or change in pressure conducive to quickly and safely dislodging a foreign object from an airway of Choking Victim 210, or otherwise resolving a choking incident, without causing further discomfort, damage, or injury.

Chamber 130 may couple to a power source such as Battery Pack 170, Wall Plug 190, or Power Converter 180, which may comprise an alternating current (AC) to direct current (DC) converter to allow the system to run off the battery independently. In another implementation, Blockage Removal 100 may operate by other power sources, for example, solar power. The power source may couple to various components of Blockage Removal by Wires 185, through which electricity may pass. In another implementation, components of Blockage Removal 100 or other devices may communicate wirelessly.

In another implementation, Blockage Removal 100 may include Viewing Means 220, for example, a translucent material of Mouthpiece 110, a light, magnifier, camera, or display screen to see inside a blocked passageway, for example, an obstructed airway, while using a Blockage Removal 100 device.

In yet another implementation, Blockage Removal 100 may provide a means for cleaning, filtering, or removing waste or objections from Blocking Removal 100 device or its components; for example, it may include a screen or Filter 230. In yet another implementation, Blockage Removal 100 may provide visual or audio prompts or instructions.

FIG. 3 illustrates a flow diagram of a process utilizing a Blockage Removal process, according to one embodiment.

At Power Source Activated 310, a user may press a button, move a switch, send a voice-activated command, or execute another means to enable power to a Blockage Removal device. The user may be a rescuer, bystander, or choking victim using the device on one's self, for example. The power source may comprise electrical, solar, or another type of power.

At Mouthpiece Secured to Choking Victim 320, an inlet equipped with a mouthpiece may be placed over an opening, for example, a mouth of the choking victim. The mouthpiece may create a fluid-tight seal to prevent interference with the vacuum or to achieve full or proper suction.

At Vacuum Pump Creates Vacuum in Chamber 330, the vacuum pump may utilize an impeller which uses centrifugal force to generate vacuum in the chamber. In another embodiment, the vacuum may generate a positive displacement of volume, for example.

At Transducer Senses Vacuum, Sends Info to ECU 340, the pressure transducer may sense an amount of vacuum in the chamber, for example, an amount in units of millimeters of mercury (mmHg). The transducer may send the vacuum information to the ECU.

At ECU Receives Vacuum Info, Sends Vacuum Info to Solenoid Valve 350, the ECU may display the vacuum information on a pressure read-out and send the information to the solenoid valve. At Solenoid Valve Opens, Exposes Vacuum 360, the solenoid valve may open at a predetermined setting, instantly exposing the vacuum. The vacuum may allow Blockage Removal to achieve an instantaneous jolt or change in pressure conducive to quickly and safely removing an obstruction from a passageway, for example, dislodging a foreign object from an airway of a choking victim, or otherwise resolving a choking incident without causing further discomfort, damage, or injury.

At Solenoid Valve Closes, Blocking Vacuum 370, the solenoid valve may close at a predetermined setting, at least temporarily blocking the vacuum. The Blockage Removal process may repeat at Vacuum Pump Creates Vacuum in Chamber 330. For example, the cycle may start again at 10-second intervals or any other duration, or until full vacuum has been achieved, a victim's airway has been cleared, an obstruction has been removed, or choking has been resolved.

The invention claimed is:
1. A device, consisting of:
an inlet;

a mouthpiece disposed on the inlet wherein the mouthpiece includes at least one of a viewing means of a magnifier, a fluid-tight seal, or an anti-microbial material;

a chamber, the chamber configured to hold a vacuum, wherein the vacuum comprises air pressure lower than atmospheric pressure;

a vacuum pump, the vacuum pump configured to create the vacuum in the chamber;

a computer;

a transducer, the transducer configured to sense the vacuum inside the chamber and configured to communicate information regarding the vacuum to the computer;

the computer is configured to communicate with another device;

a solenoid valve, the solenoid valve configured to use electricity to instantaneously open or close, wherein the opening or closing of the solenoid valve exposes or blocks the vacuum, and wherein the opening of the solenoid valve is configured to remove an obstruction from a passageway, wherein the computer has a plurality of settings related to factors from the list containing a victim's condition and a victim's characteristics; and a power source.

2. A device, consisting of:

an inlet;

a mouthpiece disposed on the inlet wherein the mouthpiece includes a viewing means of a camera;

a chamber, the chamber configured to hold a vacuum, wherein the vacuum comprises air pressure lower than atmospheric pressure;

a vacuum pump, the vacuum pump configured to create the vacuum in the chamber;

a computer;

a transducer, the transducer configured to sense the vacuum inside the chamber and configured to communicate information regarding the vacuum to the computer;

the computer is configured to communicate with another device;

a solenoid valve, the solenoid valve configured to use electricity to instantaneously open or close, wherein the opening or closing of the solenoid valve exposes or blocks the vacuum, and wherein the opening of the solenoid valve is configured to remove an obstruction from a passageway, wherein the computer has a plurality of settings related to factors from the list containing a victim's condition and a victim's characteristics; and a power source.

3. A device, consisting of:

an inlet;

a mouthpiece disposed on the inlet wherein the mouthpiece includes a viewing means of a display screen;

a chamber, the chamber configured to hold a vacuum, wherein the vacuum comprises air pressure lower than atmospheric pressure;

a vacuum pump, the vacuum pump configured to create the vacuum in the chamber;

a computer;

a transducer, the transducer configured to sense the vacuum inside the chamber and configured to communicate information regarding the vacuum to the computer;

the computer is configured to communicate with another device;

a solenoid valve, the solenoid valve configured to use electricity to instantaneously open or close, wherein the opening or closing of the solenoid valve exposes or blocks the vacuum, and wherein the opening of the solenoid valve is configured to remove an obstruction from a passageway, wherein the computer has a plurality of settings related to factors from the list containing a victim's condition and a victim's characteristics; and a power source.

* * * * *